United States Patent
Tran et al.

(10) Patent No.: US 7,089,802 B2
(45) Date of Patent: Aug. 15, 2006

(54) METHOD AND APPARATUS FOR DETERMINING HYDROGEN EMBRITTLEMENT

(75) Inventors: Luong M Tran, Tacoma, WA (US); Eric R Barta, Gig Harbor, WA (US); Matthias P Schriever, Auburn, WA (US)

(73) Assignee: The Boeing Company, Chicago, IL (US)

( * ) Notice: Subject to any disclaimer, the term of this patent is extended or adjusted under 35 U.S.C. 154(b) by 19 days.

(21) Appl. No.: 10/656,094

(22) Filed: Sep. 5, 2003

(65) Prior Publication Data

US 2005/0050961 A1    Mar. 10, 2005

(51) Int. Cl.
*G01N 3/24* (2006.01)

(52) U.S. Cl. .......................................... 73/851; 73/849

(58) Field of Classification Search ................ 73/799, 73/788, 789, 808, 809, 810, 811, 812, 849, 73/853, 851; 72/7

See application file for complete search history.

(56) References Cited

U.S. PATENT DOCUMENTS

| | | | | |
|---|---|---|---|---|
| 4,233,849 A * | 11/1980 | Defebvre et al. | ............. | 73/812 |
| 4,358,962 A * | 11/1982 | Ashby et al. | ................ | 73/849 |
| 4,408,471 A * | 10/1983 | Gossard et al. | ............. | 72/21.1 |
| 4,488,444 A * | 12/1984 | Weidmann et al. | .... | 73/862.452 |
| 4,573,360 A * | 3/1986 | Yoneda | ........................ | 73/850 |
| 4,687,106 A * | 8/1987 | Prins | .......................... | 209/552 |
| 4,691,576 A * | 9/1987 | Schleuniger et al. | .......... | 73/821 |
| 4,763,528 A * | 8/1988 | Bouami et al. | ............... | 73/799 |
| 4,864,867 A * | 9/1989 | Manahan, Sr. | ................ | 73/851 |
| 4,962,654 A * | 10/1990 | Zbornik | ...................... | 72/16.7 |
| 5,127,778 A * | 7/1992 | Scheer | ....................... | 409/132 |
| 5,156,053 A * | 10/1992 | Shiraishi et al. | .............. | 73/849 |
| 5,178,017 A * | 1/1993 | Dinzburg | ...................... | 73/849 |
| 5,277,069 A * | 1/1994 | Cussac et al. | ................ | 73/853 |
| 5,483,750 A * | 1/1996 | Ooenoki et al. | ............. | 72/17.1 |
| 5,503,024 A * | 4/1996 | Bechtel et al. | ................ | 73/852 |
| 5,505,095 A | 4/1996 | Raymond | | |
| 5,549,007 A | 8/1996 | Raymond | | |
| 5,574,227 A * | 11/1996 | Allan | .......................... | 73/849 |
| 5,585,570 A | 12/1996 | Raymond | | |
| 6,553,803 B1 * | 4/2003 | Heingartner et al. | ......... | 72/31.1 |
| 6,651,472 B1 * | 11/2003 | Chebbi | ....................... | 72/31.1 |
| 6,799,472 B1 * | 10/2004 | Nakayama et al. | ........... | 73/827 |
| 6,931,942 B1 * | 8/2005 | Uhlik et al. | .................. | 73/853 |
| 2003/0084730 A1 * | 5/2003 | Komine et al. | ............... | 73/798 |

OTHER PUBLICATIONS

AESF, 2002 Hydrogen Embrittlement Seminar, Jan. 30, 2003, 2 Pages.
ASTM International, Standard Test Method for Measurement of Hydrogen Embrittlement Threshold in Steel by the Incremental Step Loading Technique, 2003, pp. 1-5.
ASTM International, Standard Test Method for Mechanical Hydrogen Embrittlement Evaluation of Plating Processes and Service Environments, 2003, pp. 1-12.
Corrosion Source, Slow Strain Rate Testing, 2000, 1 Page.
The European Standard BS EN 2831, Hydrogen embrittlement of steels—Test by Slow bending, Feb. 1993.

* cited by examiner

*Primary Examiner*—Max Noori
(74) *Attorney, Agent, or Firm*—Harness Dickey & Pierce P.L.C.

(57) ABSTRACT

A method and apparatus for determining failure of a test component. The apparatus, according to a selected method, is able to determine the embrittlement potential of a selected procedure for a selected material. The apparatus is able to determine the embrittlement potential in a substantially quick and non-human fallible manner.

29 Claims, 4 Drawing Sheets

METHOD AND APPARATUS FOR DETERMINING HYDROGEN EMBRITTLEMENT

FIELD

The present invention relates generally to a method and apparatus for testing components, and particularly to precisely determine a fracture angle of a test component to determine embrittlement potential.

BACKGROUND

Metal components generally include various selected amounts of ductility, strength, internal stresses, and other generally known physical characteristics. These characteristics may be measured using various techniques, such as stress testing and embrittlement testing to determine and measure the various physical characteristics of the metal. Also, various standards have been determined, such that testing results can be compared to other metal components.

Various processes, which are performed on the metal, may change the physical characteristics and require re-testing or determining of whether the processes have altered the known characteristics. For example, a particular metal or metal alloy component may be chosen depending upon its known physical characteristics. Nevertheless, these known physical characteristics can be altered by processing the metal, such as painting, heating, cleaning, and other various prostheses that use various chemicals.

One form of degradation or activity that may alter the physical characteristics of a metal is hydrogen embrittlement. Generally, hydrogen embrittlement occurs when hydrogen ions are able to migrate into the crystal structure of the metal and alter it. For example, water or other chemical species may break down into ionic components, thus releasing ionic hydrogen. The ionic hydrogen may enter the metal and collect therein or destroy bonds of the various metallic ions. The collection of the hydrogen ions or the degradation of the metallic bonds alters the physical characteristics of the metal or metal alloy. Therefore, the physical characteristics may be substantially changed, thus no longer providing a material of known physical characteristics.

Therefore, it is desirable to determine whether a particular chemical process alters or has altered a metal component. For example, hydrogen embrittlement may make a metal less ductile and therefore able to endure less stress before cracking and reducing the strength of the metal. Therefore, it may be desirable to determine before a component is formed of a particular material whether that material is subject to hydrogen embrittlement because of a certain chemical process to be applied to the material.

Generally, hydrogen embrittlement may be determined by testing an unprocessed metal test blank and testing a processed metal blank or test component. One example is ASTM F-519, which determines embrittling potential of a selected process. Using the ASTM standard, both a chemically treated or processed and non-chemically treated or unprocessed metal specimen is tested to determine whether a significant difference between the component, which has been processed and the component, which has not been processed. The system, however, generally requires an extended period of time and at least 200 hours for the test to be completed. Several days must be dedicated before the determination of embrittlement potential of a selected process. Therefore, it is desirable to provide a process that is generally quicker and cheaper than such an extensive test.

Another standard is the European Standard EN2831, as described in Hydrogen Embrittlement of Steels-Test by Slow Bending, USEN 2831:1933, which is incorporated herein by reference, describes a standard and test for determining embrittlement of metal components. Generally, in the European Standard EN2831, a metal component is tested without being processed and another component is tested after being processed. The components are bent, generally manually, to induce cracking of the component. A visual determination is made to determine the failure of the component and the propagation of a crack. After a crack appears the angle the component has reached is hand measured to determine a bend angle. If the bend angle between the processed and unprocessed component is substantially different, then where the processed component includes a smaller bend angle, then the process is determined to embrittle the metal. The difference in the bend angle can be used to determine a selected embrittlement potential. Nevertheless, such a standard is generally subjective to human perception and error of both the crack and the measured angle. Nevertheless, such a bending test can be used to determine a selected hydrogen embrittlement potential.

SUMMARY

A method and apparatus to determine hydrogen embrittling or embrittlement potential using a substantially automated process have been developed. The apparatus generally includes a control module and a bending module. The control module can be used to control the bending module according to programmable and selectable variables or modes. Various modes include continuous bending, single or multiple pause in the bending for applying static load, a variable static loading time, and other possible modes. In addition, data can be gathered using any of the selected modes to provide an output. The outputs may include at the various steps or increments of time the torque or force measured from the bending apparatus, the angle at which a crack occurs (as described herein), and the time of the test. The control module can store the data internally, store the data in a volatile memory for a selected amount of time, or the data may be transferred to a computer or storage assembly for later analysis.

The bending module is generally able to engage a selected test component and bend the selected test component as controlled by the control module. The bending module may include a fixed and movable jaw or chuck that allows for bending of the selected component. Various sensors can determine the angle of the movable jaw relative to the fixed jaw and the forces measured between the two jaws as the test component is bent.

Therefore, the method and apparatus of determining hydrogen embrittlement is not subjected to human error. Generally, the bending module includes sensors that are able to determine the angle, the force or torque produced by bending the component, and changes in the same. Therefore, the failure of the component is generally non-subjectively determined and the angle of the bend can also be automatically and non-subjectively determined. Therefore, the bending apparatus can bend the component at a selected rate and quickly determine the failure of the component, thereby providing a quick and non-subjective test mechanism to determine hydrogen embrittlement or embrittlement potential of a selected process.

Further areas of applicability will become apparent from the detailed description provided hereinafter. It should be understood that the detailed description and various examples, while indicating the various embodiments are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF VARIOUS EMBODIMENTS

The following description of various embodiments is merely exemplary in nature and is in no way intended to limit the invention, its application, or uses.

Figure 1:
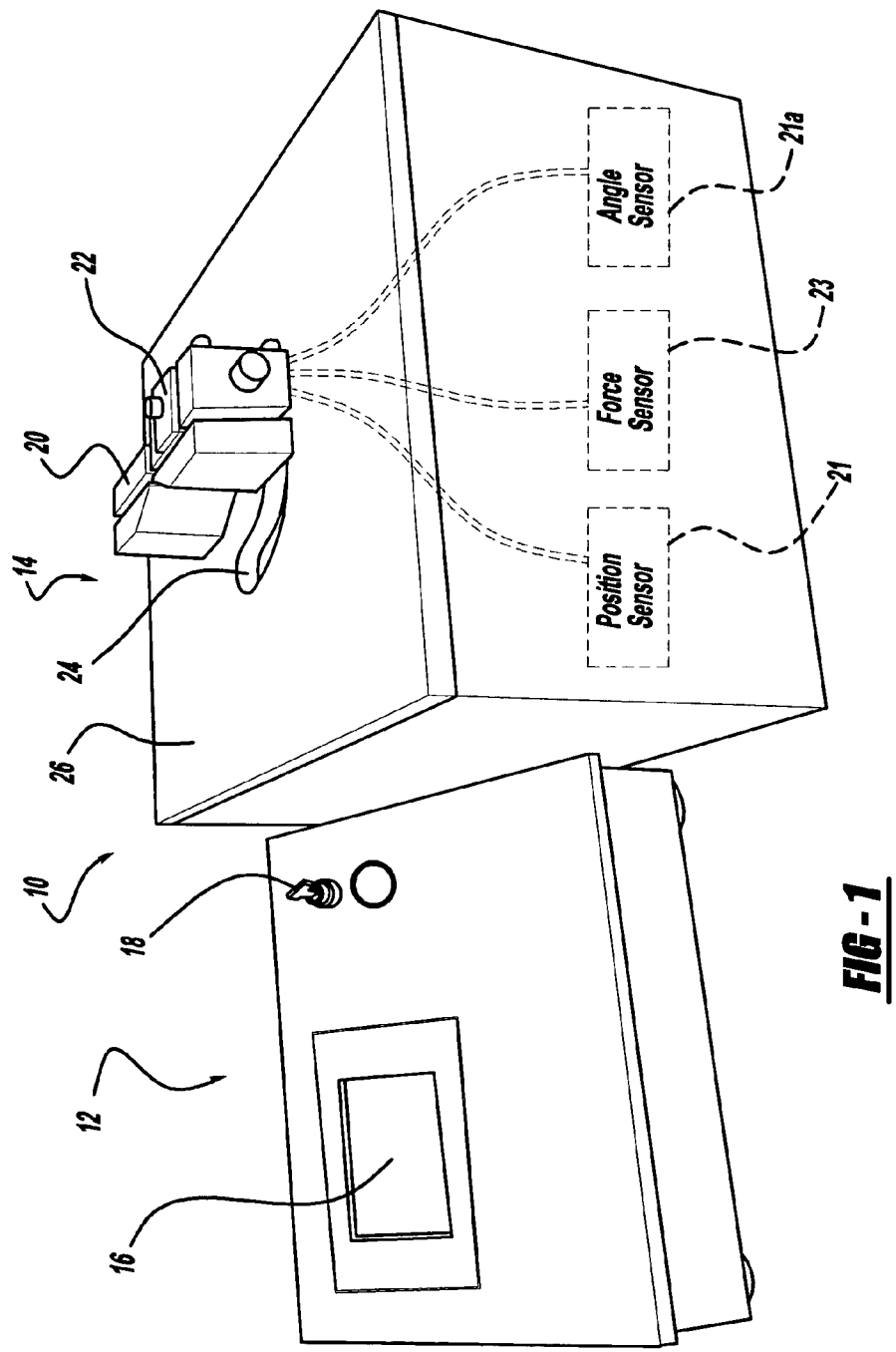
FIG. 1 is a environmental view of a test apparatus.

With reference to FIG. 1, a hydrogen embrittlement testing apparatus 10 is illustrated. The hydrogen embrittlement testing apparatus or machine (HETM) 10 generally includes a control module 12 and a moving or bending module 14. The control module 12 is able to control the bending module 14 in a selected manner to perform the test of embrittlement or embrittlement potential for a selected test component. The control module 12 may be any appropriate control module, but may generally include circuitry that is able to be programmed to control the bending module 14 in a selected manner. One generally skilled in the art will understand the circuitry and processes necessary to allow a user to program the control module to control the bending module 14. The control module 12 may include a display screen 16. The display screen 16 may include a touch screen so that an operator may operate and program the control module 12 with the screen 16. The control module 12 and the bending module 14 are controlled by a key-operated ON/OFF switch 18, such that the bending module 14 is not accidentally operated. As described herein, the bending module 14 is generally powerful and able to bend metal at a selected and programmable characteristic. Various characteristics include a bending rate (degree per minute), the bending angle between pause (step per increment), a pause rate (delay), and a pause frequency (number of pauses).

The control module 12 may be controlled with the display screen 16. Therefore, a user may determine or select various characteristics as to how that the control module 12 will control the bending module 14 through use of the touch screen 16. Nevertheless, a separate computer, such as a microcomputer, may be connected to the control module 12 to program the control module for controlling the bending module 14.

The bending module 14 includes a fixed clamp or chuck 20 and a movable clamp or chuck 22. The fixed chuck 20 is fixed relative to the bending module 14, such that a component may be fixed within the fixed chuck 20 and held in a selected position. The movable chuck 22 is generally able to move through a selected position, such as along an aperture 24 formed in a case 26 of the bending module 14. The aperture 24 allows the movable chuck 22 to be operated by a mechanism contained within the case 26 of the control module 14 to move a component through a selected range of motion relative to the fixed chuck 20.

Figure 3:
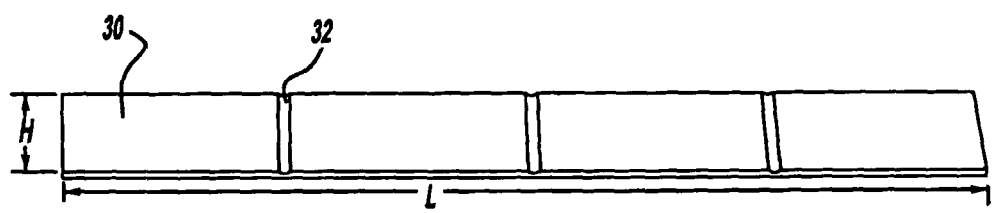
FIG. 3 is an illustration of a prepared test component.

With reference to FIG. 3, a test component or specimen 30 (later also referred to as an unprocessed specimen 30) may include a selected material, such as a nickel-based alloy or a low alloy steel AISI 4340. The test specimen 30 may be of any appropriate shape or size, but generally includes a rectangular shape that includes a height H of generally less than a length L of the test specimen 30. Formed along the length L of the test specimen 30 is at least a notch or depression 32. The depression 32 has formed a selected depth within the test specimen 30 along the entire height H of the test specimen 30. The depression 32, as described herein, generally allows for a selected or determinable cracking of the test specimen 30. The test specimen 30 may include a plurality of similar specimen. Also, a chemically treated or processed test specimen 50 (FIG. 6) that has been evaluated according to the process of interest, as discussed herein.

Figure 2:
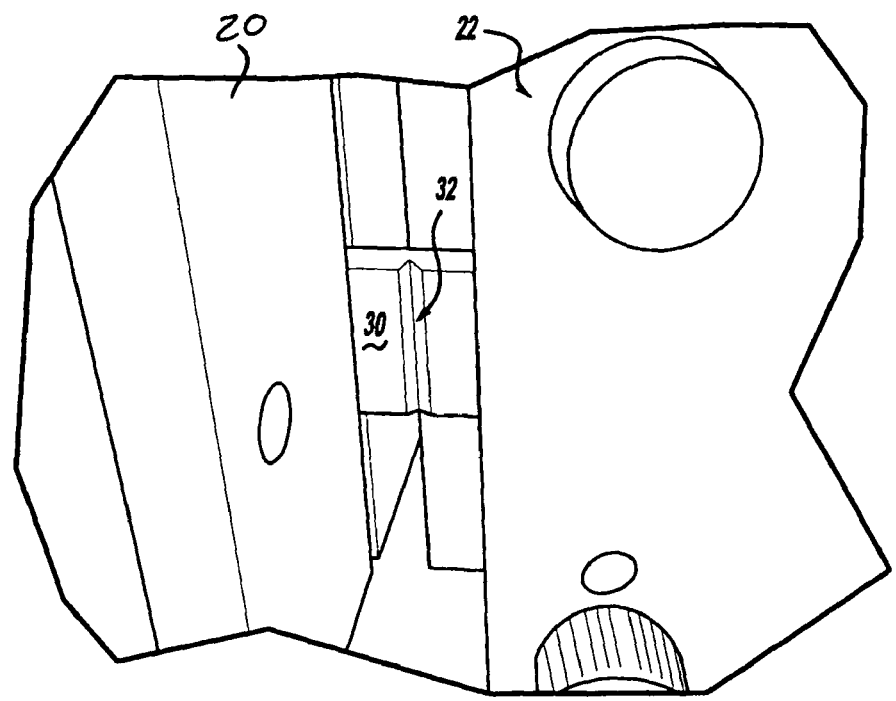
FIG. 2 is a detailed view of a component positioned in the test apparatus of FIG. 1.
Figure 4:
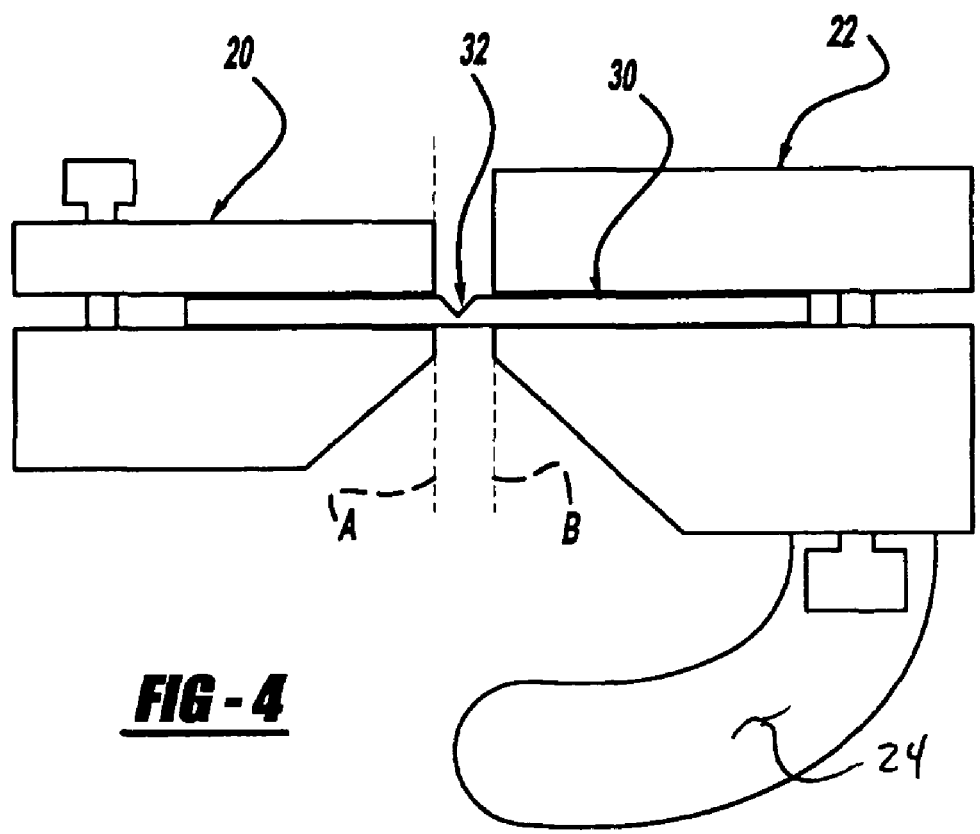
FIG. 4 is a top detailed view of a component fixed in the bending apparatus.

With reference to FIG. 4 and reference to FIG. 2, the test specimen 30 may be positioned and fixed in the fixed chuck 20 and the movable chuck 22. After the test specimen 30 is fixed between the fixed chuck 20 and the movable chuck 22, the movable chuck 22 may be moved by the bending module 14 according to the programmed procedure from the control module 12. The movable chuck 22 generally moves in a direction that bends the test specimen 30 away from the depression 32. Therefore, as the movable chuck 22 moves, as controlled by the control module 12, the notch 32 is expanded until the test specimen 30 fails.

The bending module 14 may include any appropriate mechanism to allow for movement of the movable chuck 22 relative to the fixed chuck 20. For example, a selected electrical motor may be geared to apply a selected force to the movable chuck 22 to move the movable chuck 22 according to the controlled pattern from the control module 12. Furthermore, various gears may be provided for mechanical advantage and force transfer. It will be understood that one generally skilled in the art will be able to conceive of a plurality of mechanism that will be able to move the movable chuck 22 relative to the fixed chuck 20.

In addition, the bending module 14 may include sensors, such as a position sensor 21 and/or an angle sensor 21a, that are internally sensible or sensed with the control module 12. The sensors are generally able to determine a position of the movable chuck 22 relative to the fixed chuck 20. In addition, the sensors are able to determine an amount of force experienced by the movable chuck 22 or the fixed chuck 20. Therefore, the mechanism to move the movable chuck 22 will also be able to be controlled and determine a selected force applied to the movable chuck 22 or the fixed chuck 20 according to methods described herein.

With reference to FIG. 1 and FIG. 4, a test specimen 30 is formed of a selected metal or alloy, such as a nickel-based alloy. Although it will be understood that any appropriate material may form the test specimen 30. The test specimen 30 also has formed therein the notch 32, as discussed above. The test specimen 30 is held between the fixed chuck 20 and the movable chuck 22. The test specimen 30 is initially generally aligned along a selected axis, along the length of the test specimen 30. In addition, the fixed chuck 20 defines a plane or line A and the movable chuck 22 defines a line or plane B. In an initial or unmoved position, the lines A and B are substantially parallel. Therefore, the initial test condition provides no external stress to the test specimen 30 besides the clamping force to hold the test specimen 30 in the fixed chuck 20 and the movable chuck 22.

To determine a baseline of an unaltered test specimen, a first test specimen 30 that has not been chemically treated or processed is used. That is the material of the test specimen 30 is unaffected by any chemical process of interest. A failure or cracking angle is then determined for, as described herein, the initial test specimen 30.

Figure 5:
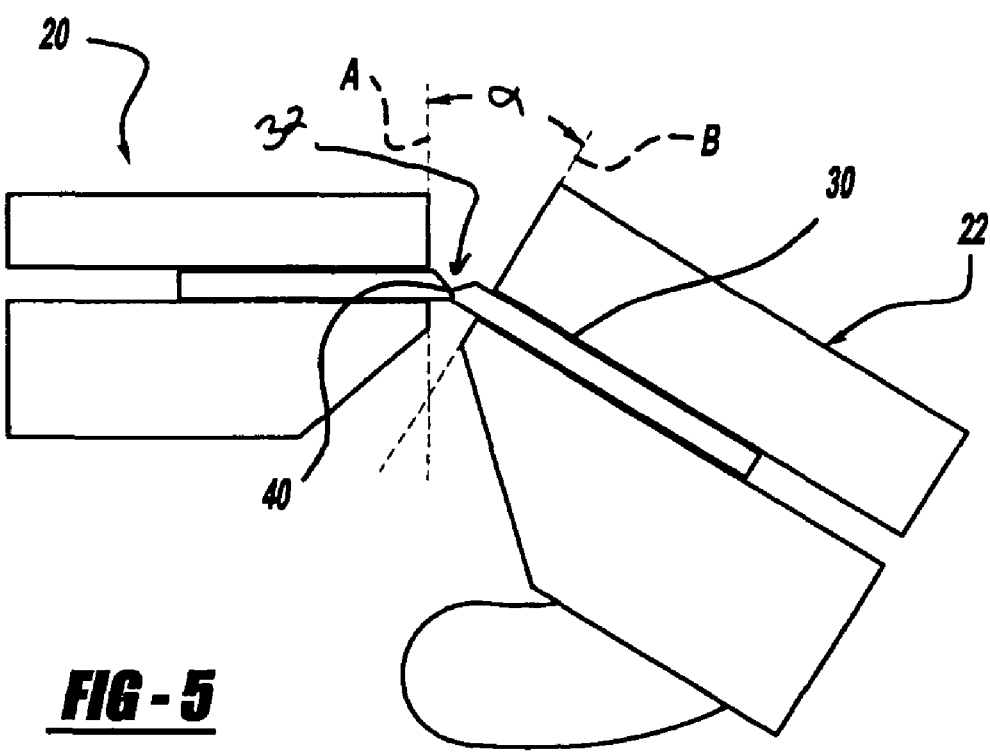
FIG. 5 is an exemplary view of a test ending status of a test component according to an embodiment.

With reference to FIG. 5, the process for determining the cracking or failure for the unprocessed specimen 30 is illustrated. The movable chuck 22 has been moved relative to the fixed chuck 20, according to a predetermined pattern that has been programmed into the control module 12. At a particular point in the bend, a crack 40 forms relative to the notch 32 of the test specimen 30. The crack 40 forms at a particular angle baseline cracking angle $\alpha$ between the line A and the line B. The movable chuck 22 has bent the unprocessed test specimen 30 to the baseline cracking angle $\alpha$ where the crack 40 has formed. The baseline cracking angle $\alpha$, is the cracking angle or cracking point of the material that is unprocessed. Therefore, processed test specimen 50 can be tested to determine whether the cracking angle is altered from the baseline cracking angle $\alpha$. It will be understood, that numerous tests, generally more than one, may be performed on a plurality of unaltered test specimen 30 to determine an average cracking angle $\alpha$ to determine the baseline cracking angle $\alpha$. Therefore, the angle $\alpha$ need not necessarily be dependent upon a single test specimen.

Figure 6:
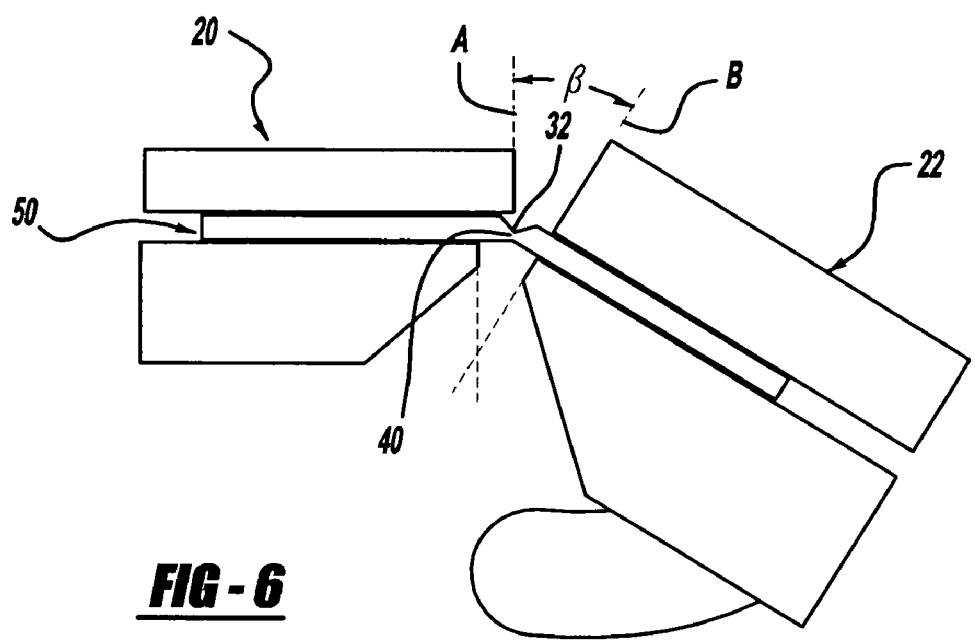
FIG. 6 is a top elevational view of an ending condition of a test component according to an alternative embodiment.

With reference to FIG. 4 and FIG. 6, a chemically treated or processed specimen 50 may be positioned in the fixed chuck 20 and the movable chuck 20, substantially similarly to the test specimen 30 as illustrated in FIG. 4. Therefore, the lines A and B are substantially parallel and no external stress is being applied to the test component 50 before the bending begins.

With reference to FIG. 6, however, a crack 52 may form in the processed test specimen 50 at a processed cracking angle $\beta$. The cracking angle $\beta$ of the processed specimen 50 is an angle between the lines A and B defined by the fixed chuck 20 and the movable chuck 22, respectively. The cracking angle $\beta$ of processed specimen 50 is the angle at which the movable chuck 22 is relative to the fixed chuck 20 when the crack 52 forms. The cracking angle $\beta$ of processed specimen 50 can be compared to the cracking angle $\alpha$ of unprocessed specimen 30 to determine whether the chemical process that has been applied to the specimen 50 has altered the angle at which the crack 52 forms in the test specimen 50. Again, it will be understood that more than one processed test specimen 50 may be tested in the bending apparatus 14 to determine an average processed cracking angle $\beta$, such that only one processed cracking angle $\beta$ data point is not used to determine the significance of the embrittlement caused by a particular chemical process or similar process that may cause hydrogen embrittlement of the specimen.

The difference between the cracking angles $\alpha$ and $\beta$ may then be used to determine the amount of embrittleness or the embrittlement potential of the processing that has been applied to the test specimen 50. The difference between cracking angles $\alpha$ and $\beta$ as whether causing significant embrittlement is at least partially dependant on the material and the process performed. For example, a ductile material may include a greater difference in a cracking angle, yet not be significantly different in weakness or embrittlement. Also, the ratio of $(\alpha-\beta)/\alpha$ may be used to determine embrittlement. Therefore, not only a raw difference but the ratio may be used to determine the emrittlement of a selected process.

One specific example of the application of the testing apparatus 10, as an application of the general process described above, is illustrated below. Generally, multiple specimens of a selected alloy or material may be obtained. A portion or sub-plurality of the multiple specimens can be used to determine the baseline breaking angle $\alpha$. According to a similar process described herein without applying a chemical process to the components. A second sub-plurality of the multiple specimens may first be cleaned and abrasive blasted according to various techniques. It will be understood that any appropriate techniques of cleaning or blasting may be used and neither are particularly necessary. Afterwards, the second plurality of components are processed according to the various chemical processes that are wished to be evaluated. For example, the embrittlement potential of a particular chemical solvent, such as for cleaning, may be understood by processing the second sub-plurality with the process prior to testing. Therefore, the second plurality or chemically treated or processed plurality of specimens will be processed according to the chemical process and with the chemical component that is to be used in practice. After the second sub-plurality are processed they can be tested, generally individually, in the testing apparatus 14. As discussed above, a computer may be attached to the control module or the control module 12 itself may be used to control the bending module 14.

A selected specimen is loaded onto the bending module 14. Generally, the test specimen 30 is loaded so that the notch 32 is positioned between the fixed chuck 20 and the movable chuck 22. Generally the notched area 32 is positioned at about 0.001 mm to about 10 mm from the edge of the fixed chuck 20. Both chucks are then tightened onto the test specimen 30 prior to moving the movable chuck 20. Generally, the movable chuck 22 is tightened last.

After the test specimen 30, or at any appropriate time before starting the bending of the test specimen, including moving the movable chuck 22, the bend test parameters can be chosen. The test parameters may be chosen using the touch screen 16 of the control module 12 or a computer that is attached to the control module 12. Various test parameters or characteristics that may be selected include bend speed. Bend speed includes the rate at which the movable chuck 22 moves relative to the fixed chuck 20, generally a degree per minute. Any appropriate bend speed may be chosen, depending upon the material of the test component 30, the time limit of the test, or desired resolution. For example, bend speeds may be about 0.0001° per minute to about 186° per second. Nevertheless, the faster the bend speed, the less precise the resolution. Although various sensors and techniques may allow for a fast bend speed with an equally high resolution.

Other test parameters may include a number of static load pauses or a pause frequency, an angle or step of movement between pauses, and a delay or time spent at a selected position. That is the movable chuck 22 may move to a selected position and stop at that position for a selected period of time. Therefore, the movable chuck 22 may move 0.5° and hold the position for ten minutes. The movable chuck 22 may then move another 0.5° and hold at that position for an additional ten minutes. Nevertheless, it will be understood that the pauses or the amount of moving between pauses may be any appropriate or selected amount. For example, a movement of about 0.0001° to about 100° may be chosen per movement. In addition, a pause time of any selected time, such as about 0.01 seconds to about twenty-four hours may be used. Also, the number of pauses may be chosen, thereby including only a number of pauses and the distance between each pause.

During the test, a load placed upon either the fixed chuck 20 or the movable chuck 22 is measured at any appropriate time step. Therefore, a load may be measured at about every 0.1 degree until the test is complete. The force placed upon the movable chuck 22 or the fixed chuck 20 is the force applied by the test specimen 30. The test component 30 should apply a generally increasing torque or load on the fixed chuck 20 or the movable chuck 22, as the movable chuck 22 continues to bend the test specimen 30. Nevertheless, when the crack 40 appears in the test specimen 30, the load that is measured on the fixed chuck 20 or the movable chuck 22 decreases. Therefore, at the time that the load is measured to decrease is substantially the angle the crack 40 occurs. The controller 12, which receives data from the force measurements, can compare it to the amount of movement that the movable chuck 22 has moved relative to the fixed chuck 20. Therefore, the angle $\alpha$ or $\beta$ can determine the step in time that the load decreases or is measured to have decreased on either the fixed chuck 20 or the movable chuck 22. It will be understood a similar process is applied to the processed test specimen 50 to determine the cracking angle $\beta$.

The data collected may then be used to determine the difference between the cracking angle $\alpha$ and the cracking angle $\beta$ to determine if the chemical process applied to the processed test specimen 50 has altered the embrittlement of the material. In addition, the data may be downloaded from the control module 12 or the computer for later use in comparison.

Generally, the data collected from the various test components is used to determine the cracking angle. During a test of the selected test specimen the position of the moveable chuck 22 relative to the fixed chuck 20 is sensed with a position or motion sensor. Therefore, the angle of the test component is determined from the position of the chucks relative to one another. Also the forces, such as a torque or other load, on each of the chucks may be sensed with a force sensor 23. The force and the position can be sensed and stored for any instant in time. Thus, when the force changes the position of the chucks and, thus, the angle of the test component may also be determined. When the force is sensed to decrease the test component may be determined to be cracked and the sensed position is used to determine the angle of the test component at the same time. The data from the sensors can be stored in a storage medium for later analysis and cracking angle determination, as well.

Therefore, the test apparatus 10 can allow for a substantially non-human monitored testing of embrittlement of a selected material. The test component can be mounted to the bending module 14 and bent according to a preprogrammed procedure until a crack occurs in the test component. The crack that occurs in the test component is determined by sensors measuring the load placed upon either the fixed chuck 20 or the movable chuck 22. Therefore, human error as to determining when a crack occurs is substantially eliminated. Also, it will be understood that the load sensors can be placed on either or both of the chucks 20, 22. Although sensors regarding the movement of the movable chuck 22 generally determine movement of the movable chuck 22 relative to the fixed chuck 20.

While various preferred embodiments have been described, those skilled in the art will recognize modifications or variations which might be made without departing from the inventive concept. The examples illustrate the invention and are not intended to limit it. Therefore, the description and claims should be interpreted liberally with only such limitation as is necessary in view of the pertinent prior art.

What is claimed is:

1. An apparatus to determine a cracking angle of a selected test component, comprising:
    a movable chuck operably movable relative to a fixed chuck in an arcuate and/or angle path to apply a load to the selected test component and according to a selected characteristic, the movable chuck operable to be coupled to the selected test component;
    a bending module operable to move said movable chuck in the path;
    a position sensor to sense the position of said movable chuck relative to said fixed chuck; and
    a control module operably controlling said bending module;
    wherein said control module is operable to select said selected characteristic.

2. The apparatus of claim 1, wherein said selected path allows said movable chuck to bend the selected test component relative to said fixed chuck in a plurality of angles.

3. The apparatus of claim 1, further comprising:
    a force sensor to sense a selected force relative to at least one of said movable chuck and said fixed chuck.

4. The apparatus of claim 3, wherein said force includes at least one of a torque, pressure, tension, and combinations thereof.

5. The apparatus of claim 1, wherein said selected characteristic includes a bend speed;
    wherein said control module selectively controls said movable chuck to move at a selected rate relative to said fixed chuck.

6. The apparatus of claim 1, wherein said selected characteristic includes pause times;
    wherein said control module controls said movable chuck to pause at a selected position for a selected period of time.

7. The apparatus of claim 1, wherein said control module controls said bending module by providing a signal to said bending module to move said movable chuck relative to said fixed chuck.

8. The apparatus of claim 1, wherein said control module and said bending module are substantially integrally formed as a single component.

9. The apparatus of claim 1, further comprising:
    a data storage apparatus operable to collect data from said position sensor as said control module controls said bending module.

10. The apparatus of claim 1, wherein said control module is operable to collect data from said position sensor to determine the position of said movable chuck relative to said fixed chuck at a selected time;
    wherein said the sensed position of said movable chuck relative to said fixed chuck allows for a determination of an angle at which the test component is bent.

11. The apparatus of claim 1, wherein said control module is user programmable to control said bending module to sense a position of said movable chuck relative to said fixed chuck and determine a bend angle of the test component when a crack forms in the test component.

12. A system to determine the cracking angle of a selected test component to assist in determining embrittlement potential of a selected process, comprising:

a bending module connected to the selected test component and operable to bend the selected test component; and a control module operable to control said bending module to select a bending characteristic of the test component;

wherein at least one of said control module, said bending module, or combinations thereof are operable to determine an angle of bending at a selected time;

wherein at least one of said control module, and said bending module, or combinations thereof are operable to determine when a crack occurs in the selected component.

13. The system of claim 12, wherein said bending module includes a first chuck and a second chuck wherein one of said first chuck and said second chuck is movable relative to the either of said first chuck and said second chuck.

14. The system of claim 13, wherein said control module controls the movement of at least one of said first chuck and said second chuck relative to said the other of first chuck and said second chuck.

15. The system of claim 13, wherein said first chuck and said second chuck are operable to be connected to the selected test component and bend the selected test component substantially according to a selected sequence provided from said control module.

16. The system of claim 12, wherein said bending characteristic includes a degree per minute, a step per increment, a delay, number of pauses.

17. The system of claim 16, wherein said a degree per minute includes the rate at which a first chuck moves relative to a second chuck;

wherein said bending module moves said second chuck per instructions from said control module.

18. The system of claim 12, wherein said maximum bend angle includes a maximum angle to which the selected test specimen is to be bent.

19. The system of claim 18, wherein said maximum bend angle is reached through a plurality of a combination of movements and pauses;

wherein the selected test specimen is bent to a selected position and held at the selected position for a selected period of time and repeated until said maximum range of motion is reached.

20. The system of claim 12, further comprising an angle sensor operable to determine the angle at which the selected test specimen is bent at a selected moment in time.

21. The system of claim 12, further comprising:
a force sensor operable to sense a force experienced by said bending module as the selected test specimen is bent by said bending module.

22. The system of claim 21, wherein said control module is able to determine the presence of the crack and the selected test specimen by the force sensed by said force sensor.

23. The system of claim 12, wherein said control module is operable to determine an angle at which the crack appears in the selected test specimen; and a least one of store the determined angle in said control module and transmit said determined angle to a storage unit.

24. The system of claim 12, further comprising:
a moveable chuck to engage and bend the test specimen relative to a fixed chuck;

a position sensor to sense the position of the moveable chuck relative said fixed chuck at a selected time; and a force sensor to sense a force experienced by said bending module at the selected time;

wherein said control module is operable to selectively record said position and said force at the selected time.

25. A system, operable to determine whether a test component has failed a test, comprising:
a first member operable to fixedly hold the test component;

a second member operable to move a portion of the test component relative to the first member, the second member connected to the test component;

a bending module operable to move the second member relative to the first member;

a control module operable to control said bending module;

a force sensor operable to determine a force exerted on at least one of the first member, the second member, or combinations thereof due to the test component positioned between the first member and the second member;

wherein said force sensor is operable to determine a force over time to determine whether the test component remains intact.

26. The system of claim 25, further comprising:
a position sensor to sense the position of the first member relative to the second member.

27. The system of claim 25, wherein said control module is operable to control the movement of the second member relative to the first member relating to a rate of movement, a number of steps of movement, a distance, or combinations thereof.

28. The system of claim 25, wherein the second member moves in an arcuate path relative to the first member.

29. The system of claim 25, wherein the second member moves in an angular path relative to the first member.

* * * * *